United States Patent [19]

Fleischhacker

[11] Patent Number: 4,519,404
[45] Date of Patent: May 28, 1985

[54] ENDOCARDIAL ELECTRODE LEAD WITH CONICAL FIXATION MECHANISM

[76] Inventor: John J. Fleischhacker, 16631 Meadowbrook La., Wayzata, Minn. 55391

[21] Appl. No.: 537,252

[22] Filed: Sep. 28, 1983

[51] Int. Cl.³ .............................................. A61N 1/04
[52] U.S. Cl. .................................. 128/785; 128/786; 128/419 P
[58] Field of Search ............................... 128/784–786, 128/419 P

[56] References Cited

U.S. PATENT DOCUMENTS

| 3,719,190 | 3/1973 | Avery | 128/785 |
| 3,935,864 | 2/1976 | Lagergren | 128/419 P |
| 4,030,508 | 6/1977 | Thalen | 128/419 P |
| 4,301,815 | 11/1981 | Doring | 128/786 |
| 4,419,819 | 12/1983 | Dickhudt et al. | 128/785 |

FOREIGN PATENT DOCUMENTS 0085967 8/1983 European Pat. Off. ............ 128/785

Primary Examiner—William E. Kamm
Assistant Examiner—Mitchell J. Shein
Attorney, Agent, or Firm—Williamson, Bains, Moore & Hansen

[57] ABSTRACT

A transvenous, endocardial heart pacemaker lead having a conical fixation device on its distal end for holding a distal tip electrode in proper pacing position within the heart. There are open spaces around the conical surface of the fixation device defined by spaced apart, circumferential rings interconnected with spaced apart ribs extending lengthwise along the conical device. Engagement of trabeculae of the heart within the open spaces and against the rings holds the lead in place.

An electrical conductor contained within an insulating sheath or catheter connects the distal tip electrode with a source of power. The conical fixation device is made out of flexible, nonconducting material.

17 Claims, 5 Drawing Figures

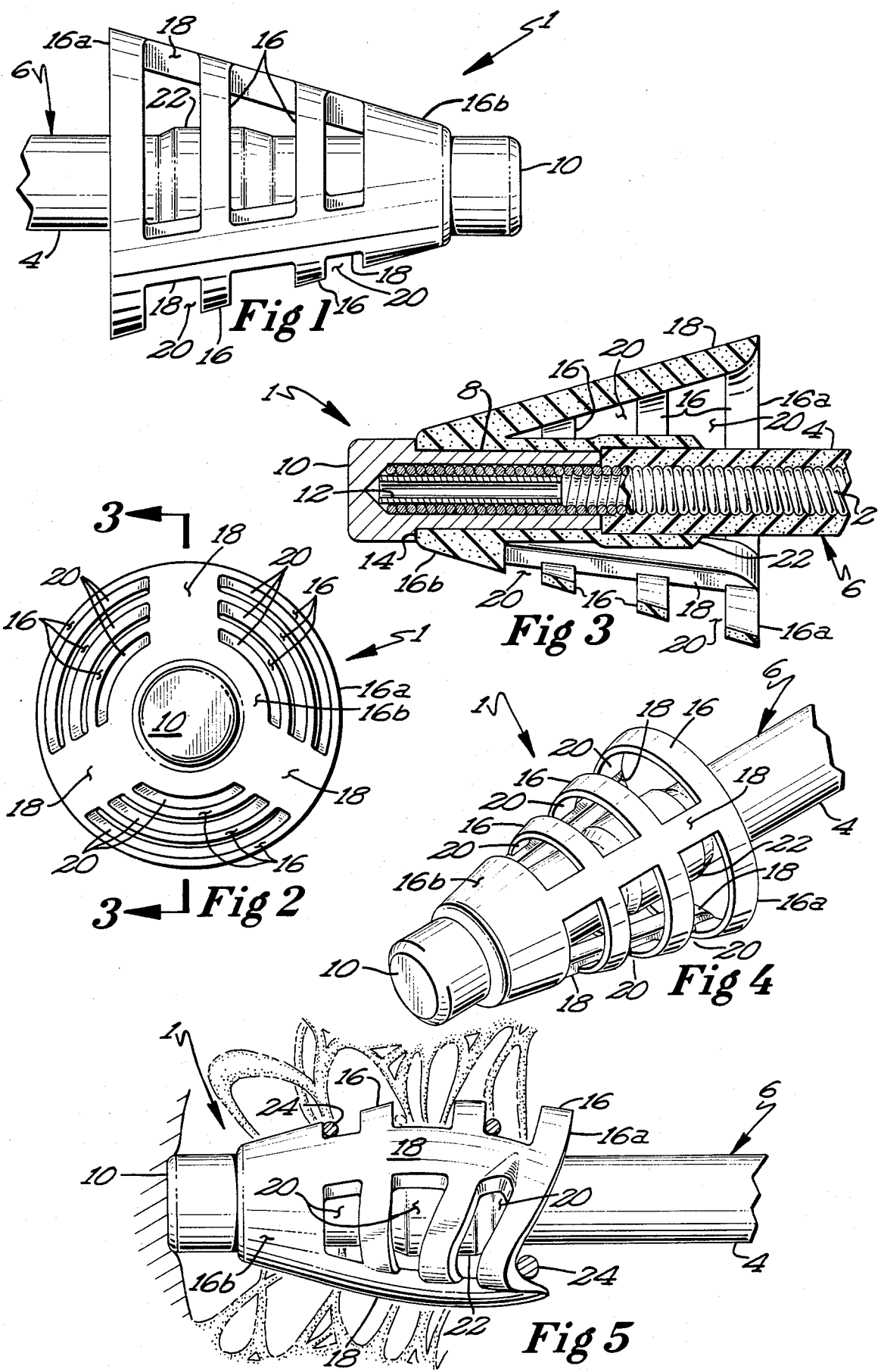

ENDOCARDIAL ELECTRODE LEAD WITH CONICAL FIXATION MECHANISM

BACKGROUND OF THE INVENTION

This invention relates to heart pacing leads of the type adapted for transvenous, endocardial implantation. Such leads are in widespread use, and normally have an exposed, distal tip electrode which is positioned against the inside surface of the heart wall. The elongated, flexible lead comprises an electrical conductor encased within an insulating sheath, and a proximal, connector end for placing the electrode in electrical connection with a pacemaker power source.

Experience has demonstrated that it is important to provide such leads with some type of fixation device for holding the tip electrode in good contact with the heart wall. Such positioning of the electrode is necessary for achieving and maintaining the desired pulse pacing of the heart. Movement or migration of the lead, with attendant dislodgement of the distal electrode, can result in disruption of pacing and/or sensing.

Various fixation mechanisms have been used on pacing leads of the aforesaid type. These include so-called active fixation devices which incorporate some means for positively securing the electrode to the endocardial surface by grasping or direct, penetrating action. Such attachment mechanisms include prongs and pincers which project forwardly from the lead distal end. U.S. Pat. No. 3,754,555 issued to Schmitt on Aug. 28, 1973 discloses leads of this type. Several exampls of leads with active fixation means are shown by E. H. Meese et al in "Initial Clinical Experience with the Ventricular Tined Lead," Proceedings of the VIth World Symposium on Cardiac Pacing. Montreal, Canada, Chapter 31-6, 1979.

The Meese et al article also discloses examples of so-called passive fixation leads, which have tines or other forms of projections such as cones with flanges to catch in the trabeculae of the heart. U.S. Pat. No. 4,030,508 issued to Thalen on June 21, 1977 discloses a conical tipped lead of the previously known type which incorporates a cone having a base flange at its proximal end. The solid cone is not collapsible and is thus made small enough to fit through the smallest size vein for transvenous introduction into the heart. The small diameter of the flange limits its anchoring ability, as is pointed out in U.S. Pat. No. 4,301,815 issued to Carl Doring on Jan. 23, 1980. That patent is directed to a so-called trailing tined lead having tines which project rearwardly from a truncated, conical tip.

Tined leads of the type having tines made from flexible, pliant material, such as silicone rubber, which extend rearwardly at an acute angle from the lead body and can yield and flex upon contact with the walls of veins during transvenous introduction, are disclosed in U.S. Pat. Nos. 3,902,501 and 4,033,357 issued to Citron et al and Helland et al, respectively. Rasor et al also disclose a tined lead in FIG. 12 of U.S. Pat. No. 3,835,864.

Tined leads suffer from the disadvantage that the tines present minimal surface area for entanglement with the trabeculae of the heart. The tines also have been known to catch in the tricuspid valve of the heart during introduction through the heart into the right ventricle.

With this background in mind, a pacemaker lead having an improved fixation mechanism for positive anchoring in the heart has been developed.

BRIEF SUMMARY OF THE INVENTION

The endocardial pacemaker lead of this invention is particularly characterized by a fixation mechanism on its distal end which may be easily inserted transvenously into the heart and which functions particularly effectively to hold a distal tip electrode in pacing contact with the inside of the heart wall.

These basic objectives are realized by providing a conical fixation device having arcuate openings and made of flexible material on the distal end of a lead comprised of an electrical condutor encased within an insulating sheath and having an exposed electrode at its distal tip. The conical fixation head is comprised of a plurality of rings circumscribing the lead in longitudinally spaced relation to each other along the length of the lead distal end and a plurality of ribs extending between and interconnected with the rings. The ribs run generally lengthwise of the conical head and define with the rings a plurality of arcuate slots within which trabeculae of the heart may become entangled and lodge against the rings.

In the preferred embodiment, the rings are spaced radially outwardly from the insulating sheath of the lead, and increase in diameter in a direction away from the exposed distal tip electrode to define a generally conical fixation head. The flexible, thin-walled material from which the conical head is formed, and the arcuate slots in it, permit it to readily collapse inwardly towards the lead insulating sheath under the constricting force of veins through which the lead is transvenously inserted.

As a particularly beneficial feature, the rings of the conical head, which may be of larger diameter than at least some of the veins through which it can be introduced into the heart, in combination with the aforesaid ribs interconnected therewith present sufficient surface area that the flow of blood acting thereon assists in the passage of the lead through veins into the heart. For the same reason, the flow of blood assists in holding the tip electrode against the inside wall of the heart. The ribs are circumferentially spaced around the rings and are preferably molded integrally therewith to form the conical fixation device.

The conical head is preferably molded from nonconducting, silicone rubber. The insulating sheath on the lead may be either silicone rubber or urethane. An inner, tubular segment on the conical head snugly embraces the lead distal end just proximal to the distal tip electrode.

These and other objects and advantages of the invention will be readily understood as the following description is read in conjunction with the accompanying drawings, wherein like reference numerals have been used to designate like elements throughout the several views.

BRIEF DESCRIPTION OF THE DRAWINGS

FIG. 1 is a side, elevation view of the distal end of a pacemaker lead incorporating the approved fixation device of this invention;

FIG. 2 is a right end view of the lead distal tip and fixation device of FIG. 1;

FIG. 3 is a vertical section view through the distal tip and fixation device taken along lines 3—3 of FIG. 2;

FIG. 4 is a perspective view showing the fixation device of this invention on the distal end of a lead; and FIG. 5 is a side elevation view similar to FIG. 1, and showing the fixation device in restraining engagement with trabeculae of the heart.

DESCRIPTION OF THE PREFERRED EMBODIMENT

With reference to the drawings, and in particular to FIGS. 1–4, the improved conical fixation device of this invention is generally indicated by reference numeral 1. As shown, fixation device 1 is mounted on the distal end of a pacemaker lead. The lead is of well known design as to its basic components, and is comprised of an elongated, flexible conductor coil 2 encased within an outer sheath or insulating covering 4. Insulating sheath 4 may be made of various materials, including silicone rubber and urethane. The lead body comprised of these two components is generally indicated by reference numeral 6.

Only the distal end of the lead is shown in the drawings. The opposite end of the lead is provided with the pin type of connector for electrical attachment of the lead to a power source. For purposes of the primary application of heart pacing for which the lead disclosed herein is intended to be used, the power source would be a pacemaker, which sends electrical pulses at a predetermined rate to the heart. The connector into the lead is basically of known design, and accordingly not been shown.

The distal end of the lead shown in FIGS. 1–4 terminates in an electrode 8 of generally tubular shape, which is attached over the outside of conductor coil 2 in electrically conductive relation thereto, by crimping or other attachment means. The distal extremity or tip 10 of electrode 8 is exposed for electrical contact with the wall of the heart. A reinforcing sleeve 12 may be inserted within the distal end of conductor coil 2 as shown in FIG. 3. The distal tip 10 of the electrode 8 is of greater diameter than the tubular, proximal end thereof and these two sections of the distal electrode 8 are separated by a shoulder 14.

Fixation device 1 is generally of conical configuration as shown. It is comprised of a plurality of interconnected rings 16 and ribs 18. Rings 16 circumscribe the lead body 6 and are longitudinally spaced along the length of lead distal end as shown. Rings 16 are of successively smaller diameter, with largest diameter ring 16a forming the base end of conical head 1 most proximally remote from distal tip electrode 10. From base ring 16a, rings 16 successively decrease in diameter along the length of the lead towards exposed electrode tip 10. In other words, rings 16 successively increase in diameter in a direction away from exposed electrode tip 10 towards the lead proximal end. Elongated ribs 18 are circumferentially spaced around rings 16 and are interconnective therewith to form an integral fixation device of generally conical shape. Ribs 18 extend generally lengthwise of the conical fixation head 1 between adjacent rings 16, and define therewith a plurality of arcuate slots or spaces 20. With fixation device 1 being of conical shape as shown, ribs 18 will project angularly with respect to insulating covering 4 and are circumferentially spaced around the outside of lead body 6.

As is clearly shown in FIGS. 1, 3, and 4, rings 16 are radially spaced outwardly from insulating sheath or covering 4. Conical fixation head is attached to lead body 6 by means of an inner, tubular segment 22 thereof. Tubular sleeve 22 is formed integrally with the proximal end 16b of conical head 1, as is shown most clearly in FIG. 3, and embraces a portion of the length of insulating covering 4 in a friction fit therewith. Tubular sleeve 22 also embraces the proximal end of tubular electrode 8 along at least a portion of its length; and the distal end of conical fixation device 1 abuts against electrode shoulder 14 as shown in FIG. 3. In this way, shoulder 14 of electrode 8 acts as a stop and locating device for conical fixation head 1. With conical fixation head 1 thus mounted and positioned on the distal end of the lead body 6, rings 16 will preferably be centered on the longitudinal axis of the lead, and will lie in planes extending generally at right angles to the longitudinal axis of lead body 6. Ribs 18 project angularly from the distal end of tubular sleeve 22, and from the distal end 16b of conical fixation head 1.

Conical fixation device 1 is preferably molded from silicone rubber. Although fixation device 1 could be molded integrally with a silicone rubber insulating covering 4, it is preferred to mold these components separately. Inner sleeve 22 may be glued to the outside of the distal end of lead insulating covering 4 by a suitable adhesive.

The silicone rubber material from which conical fixation device 1 is molded is flexible and nonconducting. The rings 16 and ribs 18 forming conical head 1 are molded with walls which are sufficiently thin that they will flex and collapse inwardly towards insulating sheath 4 under external pressure, such as that imposed by the walls of a blood vessel during transvenous implantation. A lead having the conical fixation device disclosed herein on its distal end may be implanted transvenously in accordance with well established surgical techniques. Insertion through the subclavian vein, utilizing an introducer of well known type, may readily be accomplished. The cephalic vein, or one of the jugular veins, may also be selected for transvenous introduction of the lead. The central, longitudinal passage inside of conductor coil 2 may be relied upon to accommodate a stiffening wire type of stylet to assist in the introduction of the lead, as is commonly done. If the vein through which the lead is inserted has a smaller internal diameter than the external diameter of conical fixation device 1 at its large base end 16a, conical head 1 will readily fold and collapse inwardly because of its thin walled construction to thereby permit easy passing of the lead through the vein. The conical shape of fixation device 1 presents enough surface by way of rings 16 and ribs 18 that blood flow acting on such surfaces will assist in the movement of the lead through the veins and into the heart. For the same reason, blood flow greatly assists in the movement of the distal end of the lead past the tricuspid valve of the valve into the right ventricle. Blood flow moves the conical fixation head so smoothly and easily through the tricuspid valve that there is little tendency for the lead to be caught on that valve, as could happen with tined or barbed leads.

For ventricular pacing, exposed electrode tip 10 will normally be positioned against the heart wall at the apex of the ventricle. Exposed electrode tip 10 is held in proper pacing position against the wall of the heart, as illustrated schematically in FIG. 5, by catching engagement of the trabeculae of the heart against rings 16 and within annular spaces 20. The plurality of arcuate spaces or slots 20 formed by the intersection of rings 16 and ribs 18 provides a network of spaces and surfaces within and on which trabeculae may become entangled and entrapped to securely hold exposed electrode tip 10 in proper pacing position. The trabeculae are string or threadlike tissues found in the ventricle and to a lesser extent in the atrium of the heart. Several such trabeculae are illustrated schematically by reference numeral 24 in FIG. 5. As may be noted, rings 16 provide the principal contact surfaces as is illustrated with several of the rings in FIG. 5, any tendency of the lead to move directly away from the heart wall against which electrode tip 10 is positioned (to the right as viewed in FIG. 5) will cause trabeculae bearing against the proximal edges of rings 16 to bend and flex those rings towards the distal end of the lead. As a result, the longitudinally extending ribs 18 adjacent the ring segments which are being engaged by trabeculae will tend to hook or curve inwardly towards the body 6 of the lead. The ribs 18 will thereby be caused to curl around the trabeculae to further assist in entrapping the trabeculae and holding the distal tip of the electrode in proper pacing position. This hooking action of the ribs 18 provides an active, grasping mode of fixation, in addition to the passive fixation provided by the catching and entanglement of trabeculae on rings 16 and within arcuate slots or open spaces 20. It is to be noted that slight rotation of the lead, and thus of conical fixation head 1, after the distal end of the lead is in place within the heart, can assist in catching and entangling trabeculae on the conical fixation head 1.

The engagement of trabeculae with rings 16 will normally take place only along a portion of the circumference of each ring. Since the rings are of very thin-walled, flexible material, this causes the entire ring, which is caught on a trabeculae, to be urged inwardly towards lead body 6, to some extent, as is illustrated in FIG. 5. This collapsing and folding action of the rings further assists in entrapment of trabeculae. It is also noteworthy that blood flow assists in holding the exposed electrode tip 10 against the heart wall, because of contact with the exposed surfaces of conical fixation device 1, for the same reasons set forth with respect to transvenous insertion.

Although a unipolar lead having a single electrode 8 has been disclosed herein, the conical fixation device has obvious utility for bipolar leads as well. Such leads have a second electrode, normally in the form of a ring, on the distal end of the lead, at a remote location from the distal tip electrode. It is also contemplated that the conical fixation device disclosed herein will have utility on pacing leads used for atrial pacing as well as for ventricular pacing.

It is anticipated that various changes may be made in the size, shape, and construction of the approved conical fixation device disclosed herein for transvenous leads without departing from the spirit and scope of the invention as defined by the following claims.

What is claimed is:

1. A transvenous, endocardial pacemaker lead comprising:
   an elongated electrical conductor;
   an insulating sleeve covering said conductor;
   an exposed, conductive electrode at the distal end of said lead electrically connected to said conductor;
   fixation means on the distal end of said lead for holding said lead within the heart with said electrode in conductive contact with heart tissue, comprising a conical shaped head attached to the lead around said insulating sleeve with the enlarged base end of said conical head being the portion of said head most proximally remote from said electrode, and said conical head being comprised of a plurality of rings of successively smaller diameter longitudinally spaced along the length of said lead with said rings decreasing in diameter in a direction from said base end towards said electrode, and a plurality of ribs circumferentially spaced around said rings and interconnected thereto, said ribs extending generally lengthwise of said conical head between said rings, whereby said conical head may be secured within the heart by the catching engagement of said rings with trabeculae of the heart.

2. An endocardial lead as defined in claim 1 wherein: said conical head is made of flexible, nonconducting material.

3. An endocardial lead as defined in claim 2 wherein: said rings are spaced radially outwardly from said insulating sleeve, and said rings and ribs are sufficiently thin that they will flex and collapse inwardly towards said insulating sleeve under constraining forces.

4. An endocardial lead as defined in claim 2 wherein: said conical head is molded from silicone rubber.

5. An endocardial lead as defined in claim 4 wherein: said insulating sleeve is silicone rubber.

6. An endocardial lead as defined in claim 2 wherein: said rings are spaced radially outwardly from said insulating sleeve; and
   said ribs project angularly with respect to said insulating sleeve from the distal end of said lead and define with adjacent rings a plurality of arcuate slots within which trabeculae of the heart may extend and become engaged against said rings.

7. An endocardial lead as defined in claim 6 wherein: said conical head is attached to the lead around said insulating sleeve by an inner, tubular segment of said conical head which embraces at least a portion of the length of the distal end of said insulating sleeve.

8. In an electrode lead of the type having an elongated electrical conductor contained within an insulating covering with connector means at the proximal end of the lead for electrical connection to a power source and an exposed electrode at the distal end of the lead in conductive relation to the electrical conductor, improved fixation means for holding said electrode in contact with body tissue comprising:
   a conical fixation device on said distal end of the lead made of flexible material and comprised of a plurality of rings circumscribing the lead in longitudinally spaced relation along the length of the lead distal end, said rings increasing in diameter in a direction away from said exposed electrode and towards the lead proximal end, and a plurality of ribs extending between and interconnected with said rings and circumferentially spaced around the lead, said ribs extending generally lengthwise of said conical device.

9. An electrode lead as defined in claim 8 wherein: said ribs project angularly with respect to the insulating covering of said lead and define with adjacent rings arcuate slots within which body tissue may be received and entrapped for anchoring engagement with said rings.

10. An electrode lead as defined in claim 8 wherein: said rings are centered on the longitudinal axis of said lead and are radially spaced outwardly from said insulating covering.

11. An electrode lead as defined in claim 10 wherein:
said rings lie in planes extending generally at right angles to the longitudinal axis of the lead body.

12. An electrode lead as defined in claim 8 wherein:
said conical fixation device is molded from silicone rubber.

13. An electrode lead as defined in claim 12 wherein:
said insulating covering is silicone rubber.

14. An electrode lead as defined in claim 12 wherein:
said insulating covering is made of urethane.

15. An electrode lead as defined in claim 8 wherein:
said conical fixation device further comprises an inner, tubular sleeve which embraces a portion of the length of said insulating covering in a friction fit therewith.

16. An electrode lead as defined in claim 15 wherein:
said ribs project from the distal end of said tubular sleeve.

17. An electrode lead as defined in claim 15 wherein:
said electrode is of elongated, tubular shape and has an exposed, conductive tip at its distal extremity separated by a shoulder from a proximal end of lesser diameter than said distal extremity; and the distal end of said conical fixation device abuts against said electrode shoulder with at least a portion of said inner, tubular sleeve embracing said proximal end of the tubular electrode.

* * * * *